(12) United States Patent
Gately

(10) Patent No.: US 8,641,764 B2
(45) Date of Patent: Feb. 4, 2014

(54) SPINE IMPLANT INSERTION DEVICE AND METHOD

(75) Inventor: Nicholas V. Gately, Lambertville, NJ (US)

(73) Assignee: G&L Consulting, LLC, New York, NY (US)

( * ) Notice: Subject to any disclaimer, the term of this patent is extended or adjusted under 35 U.S.C. 154(b) by 1012 days.

(21) Appl. No.: 11/870,844

(22) Filed: Oct. 11, 2007

(65) Prior Publication Data

US 2008/0091211 A1    Apr. 17, 2008

Related U.S. Application Data

(60) Provisional application No. 60/829,065, filed on Oct. 11, 2006.

(51) Int. Cl.
*A61F 2/44* (2006.01)
*A61B 17/88* (2006.01)

(52) U.S. Cl.
USPC .......................................... 623/17.16; 606/99

(58) Field of Classification Search
USPC ................... 606/99, 279; 623/17.11–17.16
See application file for complete search history.

(56) References Cited

U.S. PATENT DOCUMENTS

| | | |
|---|---|---|
| 5,609,635 A | 3/1997 | Michelson |
| 5,653,763 A | 8/1997 | Errico et al. |
| 5,713,899 A | 2/1998 | Marnay et al. |
| 5,717,006 A | 2/1998 | Daculsi et al. |
| 5,895,428 A | 4/1999 | Berry |
| 6,143,032 A | 11/2000 | Schafer et al. |
| 6,143,033 A | 11/2000 | Paul et al. |
| 6,156,037 A * | 12/2000 | LeHuec et al. ............. 606/247 |
| 6,245,108 B1 | 6/2001 | Biscup |
| 6,346,123 B1 | 2/2002 | McKay |
| 6,478,800 B1 | 11/2002 | Fraser et al. |
| 6,517,544 B1 | 2/2003 | Michelson |
| 6,537,589 B1 | 3/2003 | Chae et al. |
| 6,558,424 B2 | 5/2003 | Thalgott |
| 6,599,294 B2 | 7/2003 | Fuss et al. |
| 6,682,534 B2 | 1/2004 | Patel et al. |
| 6,719,794 B2 | 4/2004 | Gerber et al. |
| 7,018,413 B2 | 3/2006 | Kruger |
| 7,060,073 B2 * | 6/2006 | Frey et al. ..................... 606/85 |
| 7,105,023 B2 | 9/2006 | Eckman |
| 7,169,183 B2 * | 1/2007 | Liu et al. ................. 623/17.16 |

(Continued)

FOREIGN PATENT DOCUMENTS

| | | |
|---|---|---|
| WO | 98/56319 | 12/1998 |
| WO | 02/17823 | 3/2002 |
| WO | 2006/079356 | 8/2006 |

OTHER PUBLICATIONS

U.S. Appl. No. 11/278,552, filed Apr. 4, 2006.

(Continued)

*Primary Examiner* — Nicholas Woodall
*Assistant Examiner* — Larry E Waggle, Jr.
(74) *Attorney, Agent, or Firm* — Nixon & Vanderhye P.C.

(57) ABSTRACT

A spinal implant include a top, wherein at least a portion of the top is configured to contact a first vertebra, a bottom, wherein at least a portion of the bottom is configured to contact a second vertebra, a side having a releasable attachment to receive an insertion device and a cam surface to engage a cam on the insertion device.

18 Claims, 9 Drawing Sheets

(56) References Cited

U.S. PATENT DOCUMENTS

| | | |
|---|---|---|
| 7,226,483 B2 | 6/2007 | Gerber et al. |
| 7,235,082 B2 * | 6/2007 | Bartish et al. .................... 606/99 |
| 7,338,526 B2 | 3/2008 | Steinberg |
| 7,465,305 B2 * | 12/2008 | Liu et al. ......................... 606/84 |
| 7,470,273 B2 * | 12/2008 | Dougherty-Shah ......... 606/86 A |
| 7,479,160 B2 * | 1/2009 | Branch et al. ............... 623/17.11 |
| 7,500,991 B2 * | 3/2009 | Bartish et al. .............. 623/17.11 |
| 7,594,919 B2 * | 9/2009 | Peterman ........................ 606/99 |
| 7,637,953 B2 * | 12/2009 | Branch et al. ............... 623/17.11 |
| 7,959,675 B2 * | 6/2011 | Gately ........................ 623/17.11 |
| 2002/0107573 A1 | 8/2002 | Steinberg |
| 2002/0161444 A1 | 10/2002 | Choi |
| 2003/0100950 A1 | 5/2003 | Moret |
| 2004/0153065 A1 * | 8/2004 | Lim ................................ 606/53 |
| 2004/0193159 A1 | 9/2004 | Zucherman et al. |
| 2005/0004671 A1 | 1/2005 | Ross et al. |
| 2005/0027360 A1 | 2/2005 | Webb et al. |
| 2005/0096745 A1 * | 5/2005 | Andre et al. ............... 623/17.11 |
| 2005/0256578 A1 | 11/2005 | Blatt et al. |
| 2005/0283245 A1 * | 12/2005 | Gordon et al. ............. 623/17.15 |
| 2006/0129244 A1 | 6/2006 | Ensign |
| 2006/0229627 A1 * | 10/2006 | Hunt et al. ...................... 606/86 |
| 2006/0235426 A1 | 10/2006 | Lim et al. |
| 2006/0241642 A1 | 10/2006 | Arnin et al. |
| 2007/0093850 A1 | 4/2007 | Harris et al. |
| 2007/0208343 A1 | 9/2007 | Magerl et al. |
| 2007/0225726 A1 | 9/2007 | Dye et al. |
| 2007/0225805 A1 | 9/2007 | Schmieding |
| 2007/0225808 A1 | 9/2007 | Warnick |
| 2007/0282449 A1 | 12/2007 | de Villiers et al. |
| 2008/0009880 A1 | 1/2008 | Warnick et al. |
| 2008/0027544 A1 | 1/2008 | Melkent |
| 2008/0065082 A1 | 3/2008 | Chang et al. |
| 2008/0097435 A1 | 4/2008 | DeRidder et al. |
| 2008/0097454 A1 | 4/2008 | DeRidder et al. |
| 2008/0109005 A1 | 5/2008 | Trudeau et al. |
| 2008/0119935 A1 | 5/2008 | Alvarez |
| 2008/0125865 A1 | 5/2008 | Abdelgany |
| 2009/0054991 A1 | 2/2009 | Biyani et al. |
| 2009/0276049 A1 * | 11/2009 | Weiland .................... 623/17.16 |
| 2010/0094422 A1 | 4/2010 | Hansell et al. |
| 2010/0256760 A1 | 10/2010 | Hansell |

OTHER PUBLICATIONS

U.S. Appl. No. 12/000,265, filed Dec. 11, 2007.
PCT International Search Report for PCT/US2004/023721, completed Nov. 23, 2004.

* cited by examiner

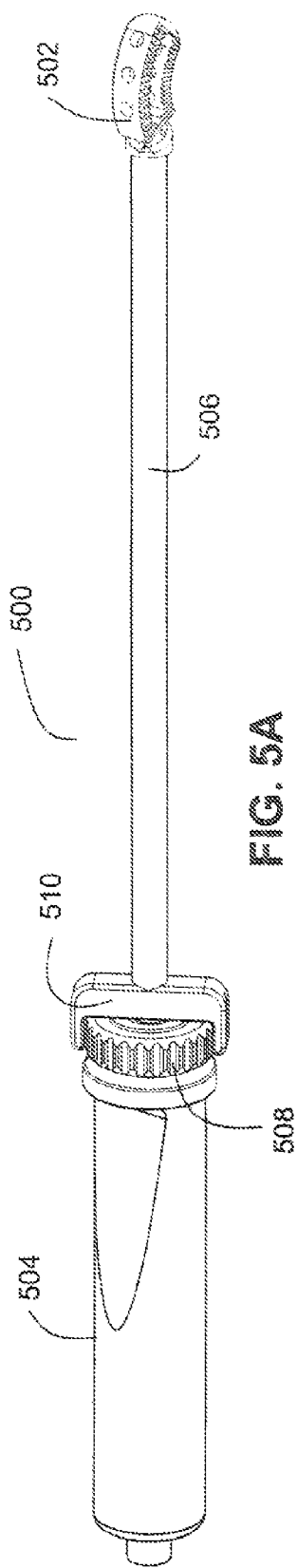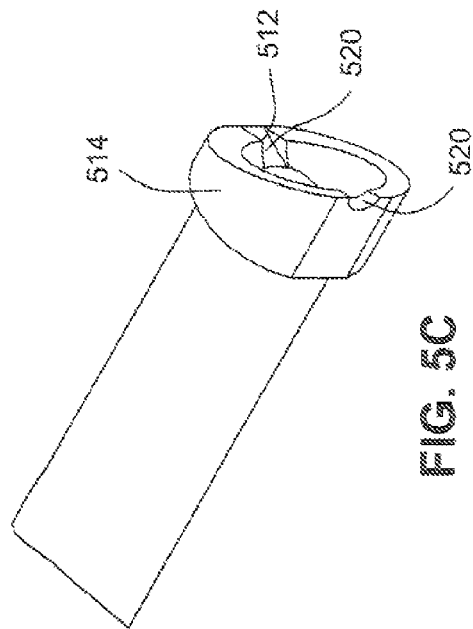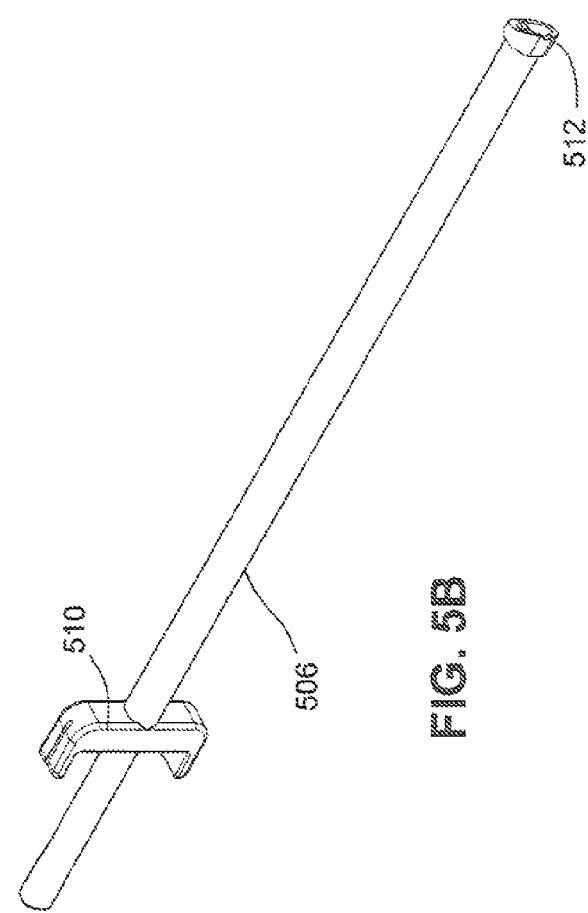

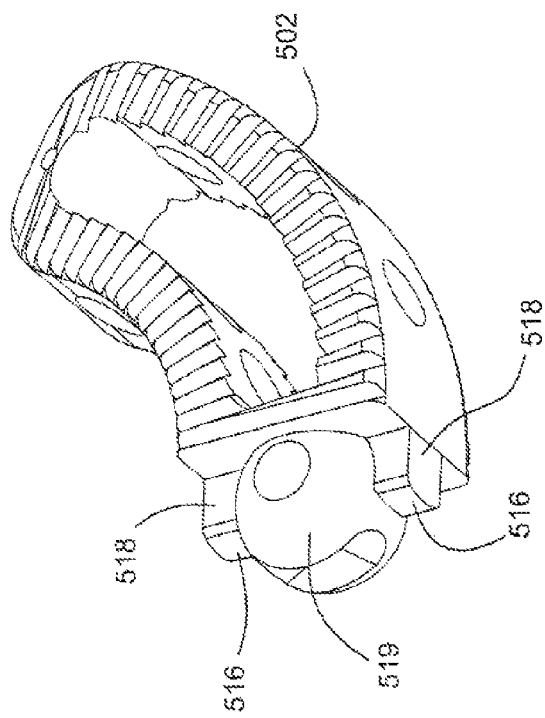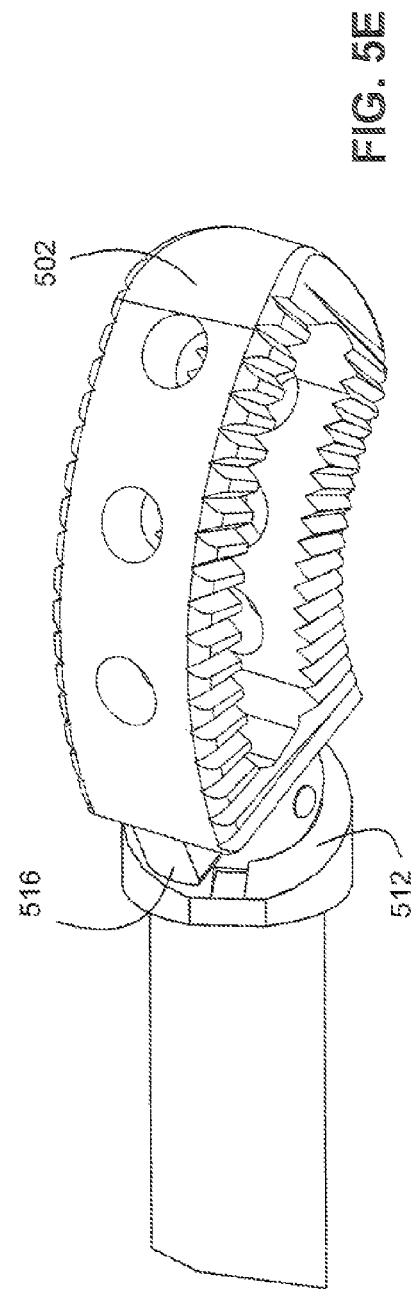

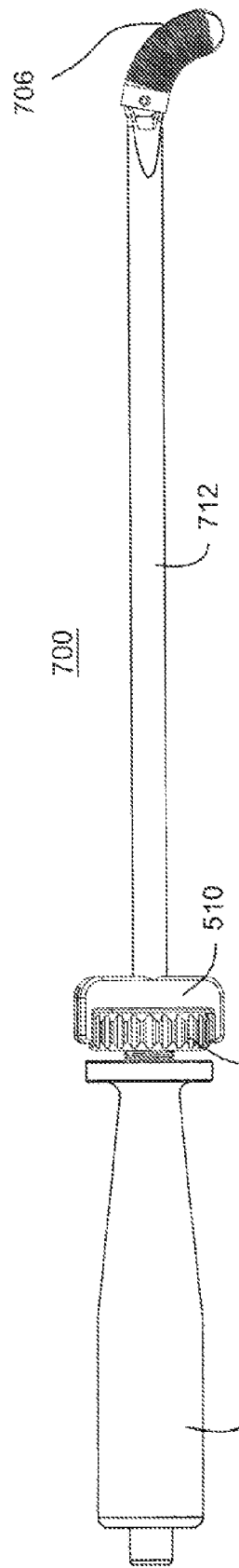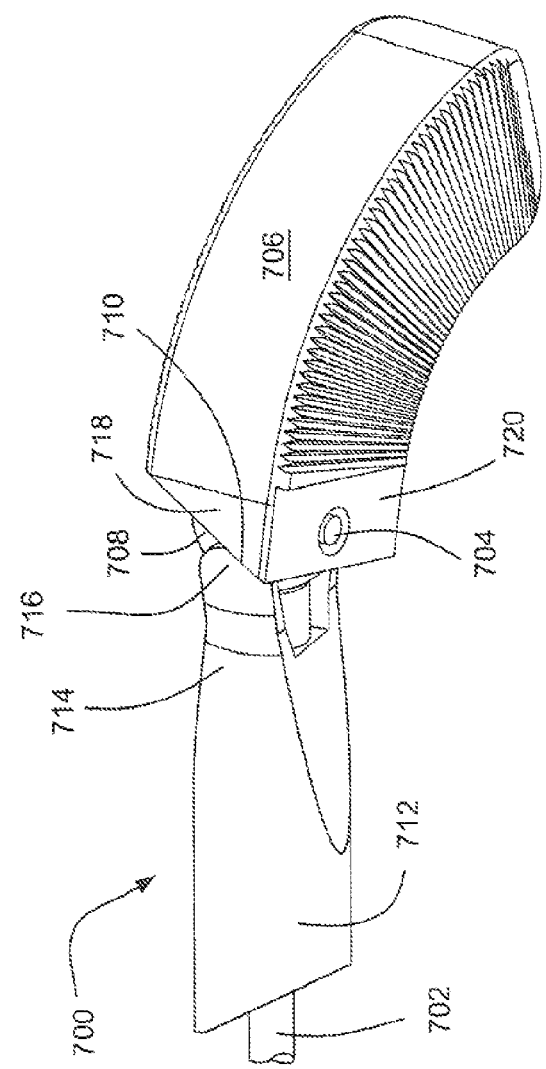

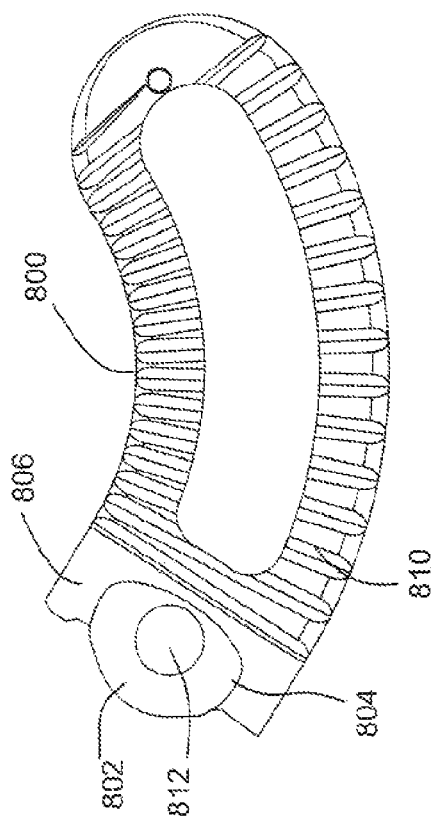
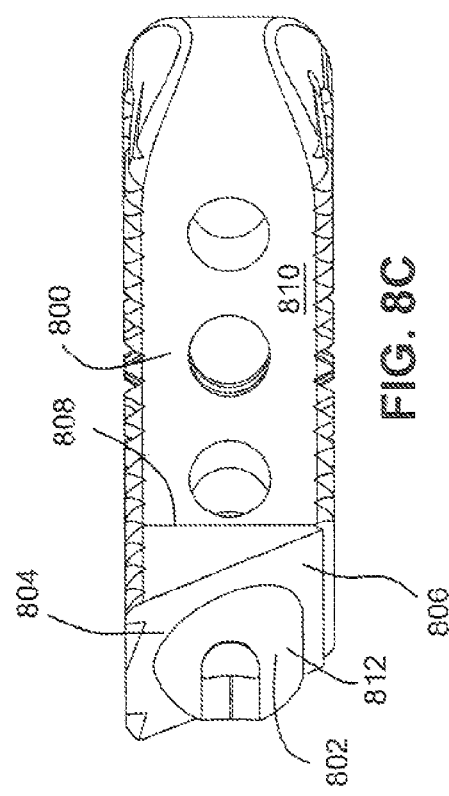
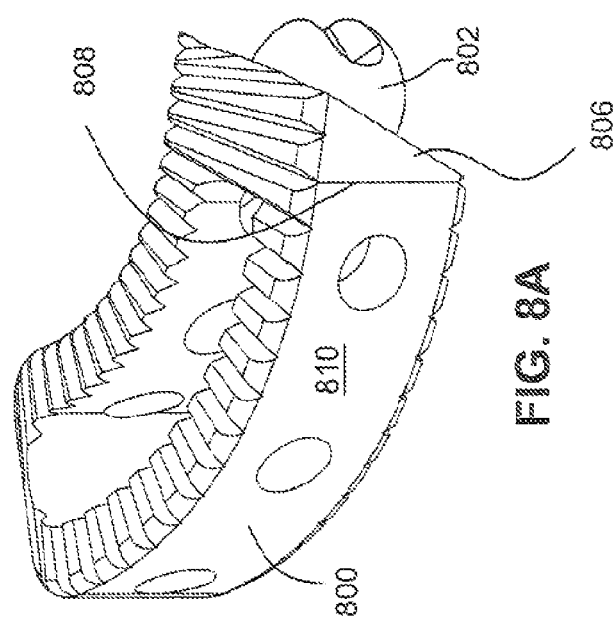

SPINE IMPLANT INSERTION DEVICE AND METHOD

This application is claims the benefit of U.S. Provisional Patent Application Ser. No. 60/829,065, the entirety of which is incorporated by reference.

BACKGROUND OF THE INVENTION

The present invention generally relates to the field of medical devices. Some embodiments of the invention relate to spinal implants inserted in the spine of a patient during surgical procedures and to instruments used to insert the implants. Other embodiments of the invention relate to methods for positioning, rotating and advancing an implant during a surgical procedure.

A spinal implant may be used to stabilize a portion of a spine. The implant may promote bone growth between adjacent vertebra that fuses the vertebra together. The implant may include a spherical protrusion, a threaded pin and an angled surface to facilitate remote adjustment of the implant position using an insertion instrument.

The insertion instrument may include, but is not limited to, a threaded rod, an actuator and a lock knob. The insertion instrument can be attached and detached to the implant, rotate the implant by transferring torque from the actuator to the implant. The actuator can be used to lock the implant in relation to the instrument. The rod can be used to apply force to the implant and advance it. The implant and instruments may be supplied in an instrument kit.

An intervertebral disc may degenerate. Degeneration may be caused by trauma, disease, and/or aging. An intervertebral disc that becomes degenerated may have to be partially or fully removed from a spinal column. Partial or full removal of an intervertebral disc may destabilize the spinal column. Destabilization of a spinal column may result in alteration of a natural separation distance between adjacent vertebra. Maintaining the natural separation between vertebra may prevent pressure from being applied to nerves that pass between vertebral bodies. Excessive pressure applied to the nerves may cause pain and nerve damage.

During a spinal fixation procedure, a spinal implant may be inserted in a space created by the removal or partial removal of an intervertebral disc between adjacent vertebra. The spinal implant may maintain the height of the spine and restore stability to the spine. Bone growth may fuse the implant to adjacent vertebra.

A spinal implant may be inserted during a spinal fixation procedure using an anterior, lateral, posterior, or transverse spinal approach. A discectomy may be performed to remove or partially remove a defective or damaged intervertebral disc. The discectomy may create a space for a spinal implant. The amount of removed disc material may correspond to the size and type of spinal implant to be inserted.

Spinal implants are described in U.S. Pat. No. 5,653,763 to Errico et al.; U.S. Pat. No. 5,713,899 to Marney et al.; U.S. Pat. No. 6,143,033 to Paul et al.; U.S. Pat. No. 6,245,108 to Biscup; and U.S. Pat. No. 5,609,635 to Michelson, U.S. patent. application 20050027360 to Webb.

BRIEF DESCRIPTION OF THE INVENTION

A spinal implant is disclosed comprising: a top, wherein at least a portion of the top is configured to contact a first vertebra; a bottom, wherein at least a portion of the bottom is configured to contact a second vertebra and a side having a releasable attachment to receive an insertion device and a cam surface to engage a cam on the insertion device. The spinal implant may include a hemispherical mount and a pin mounted within the spinal implant, wherein the insertion device attaches to the pin that serves as an axis of rotation and pivots around the pin with respect to the hemispherical housing.

A method is disclose comprising: inserting an implant between portions of bone, wherein the implant locked at a first angle relative to a shaft of the instrument; loosening the implant relative to the shaft; turning the shaft to pivot the implant relative to the shaft, and releasing the implant from the instrument so that the implant is in position between the bone. Turning the shaft rotates a cam fixed to the shaft across a cam surface on the implant, wherein the cam surface is slanted and the movement of the cam across the cam surface pivots the implant.

BRIEF DESCRIPTION OF THE DRAWINGS

FIGS. 5A, 5B, 5C, 5D and 5E show a side view of a first alternative spinal implant tool (FIG. 5A), a perspective view of the actuator for the tool (FIG. 5B), an enlarged view of the distal end of the actuator (FIG. 5C), a perspective view of the spinal implant (FIG. 5D) and an enlarged view of the distal end with a spinal implant attached to the actuator (FIG. 5E).

FIGS. 7A and 7B show a side view of a third alternative spinal implant tool (FIG. 7A), and a perspective view of the distal end of tool attached to a spinal implant (FIG. 7B).

FIGS. 8A, 8B and 8C show a perspective view (FIG. 8A), a top view (FIG. 8B) and an inner side view (FIG. 8C) of a spinal implant.

DETAILED DESCRIPTION OF THE INVENTION

Figure 1:
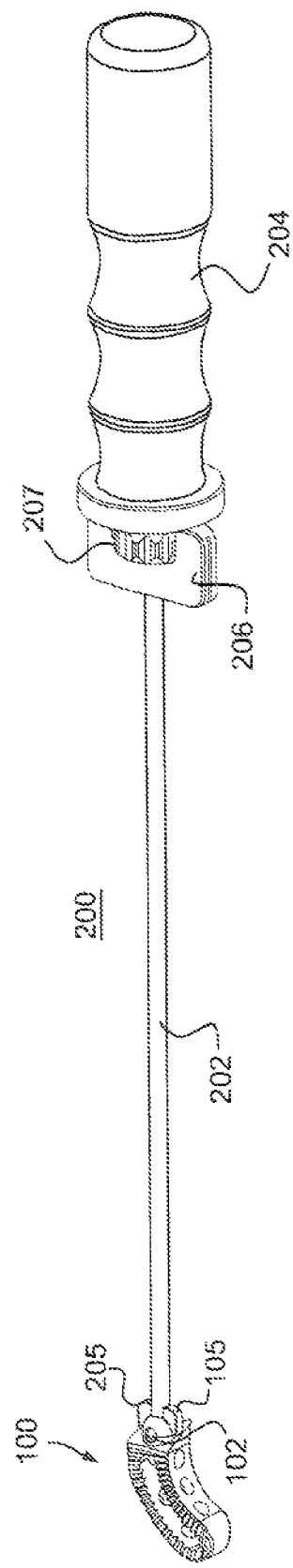
FIG. 1 is a top-side perspective view of a spinal implant attached to an insertion instrument.

FIG. 1 shows the spinal implant 100 releasably attached to an insertion instrument 200. The implant 100 may be made by made of PEEK plastic commonly used in spinal implants. The implant includes a hemispherical mount 105 and slanted cam surface 106 from which the mount protrudes. The tip of rod 201 pivotably attaches to the mount such that the implant may pivot with respect to the axis of the instrument. The pivoting of the implant is controlled by the knob on the instrument that rotates the cam wings 205 about the hemispherical surface. The rotation of the cam, slides the front edges of the cam wings across the cam surface 106 and thereby forces the implant to pivot with respect to the axis of the instrument.

A knob (e.g. actuator wings) 206 on the on the proximal end of the instrument enables a surgeon to rotate the cam and thereby adjust the angle between the implant and the axis of the instrument. Pivoting of the implant is caused as the actuator pushers 205 (e.g., cam) act on the slanted surface 106 of the implant 100. As the cammed actuator 202 rotate and slide across the slanted surface 106, the implant makes a yaw movement with respect to the axis of the instrument. Actuator 202 is equipped with the actuator wings 206 used to rotate pushers 205 (cam) from outside of the patient's body.

Locking knob 207 may be tightened to bind the actuator against the implant effectively locking the implant with respect to the instrument. When locked, axial force and torque can be applied to the handle 204 to advance the implant into the spinal space and position the implant in the space. Turning the locking knob 207 that is threaded inside and engages threads on the proximal end of the rod causes the actuator 202 that is hollow to slide axially forward over the threaded rod 201 and thereby loosen or tighten the actuator against the implant.

Figure 2:
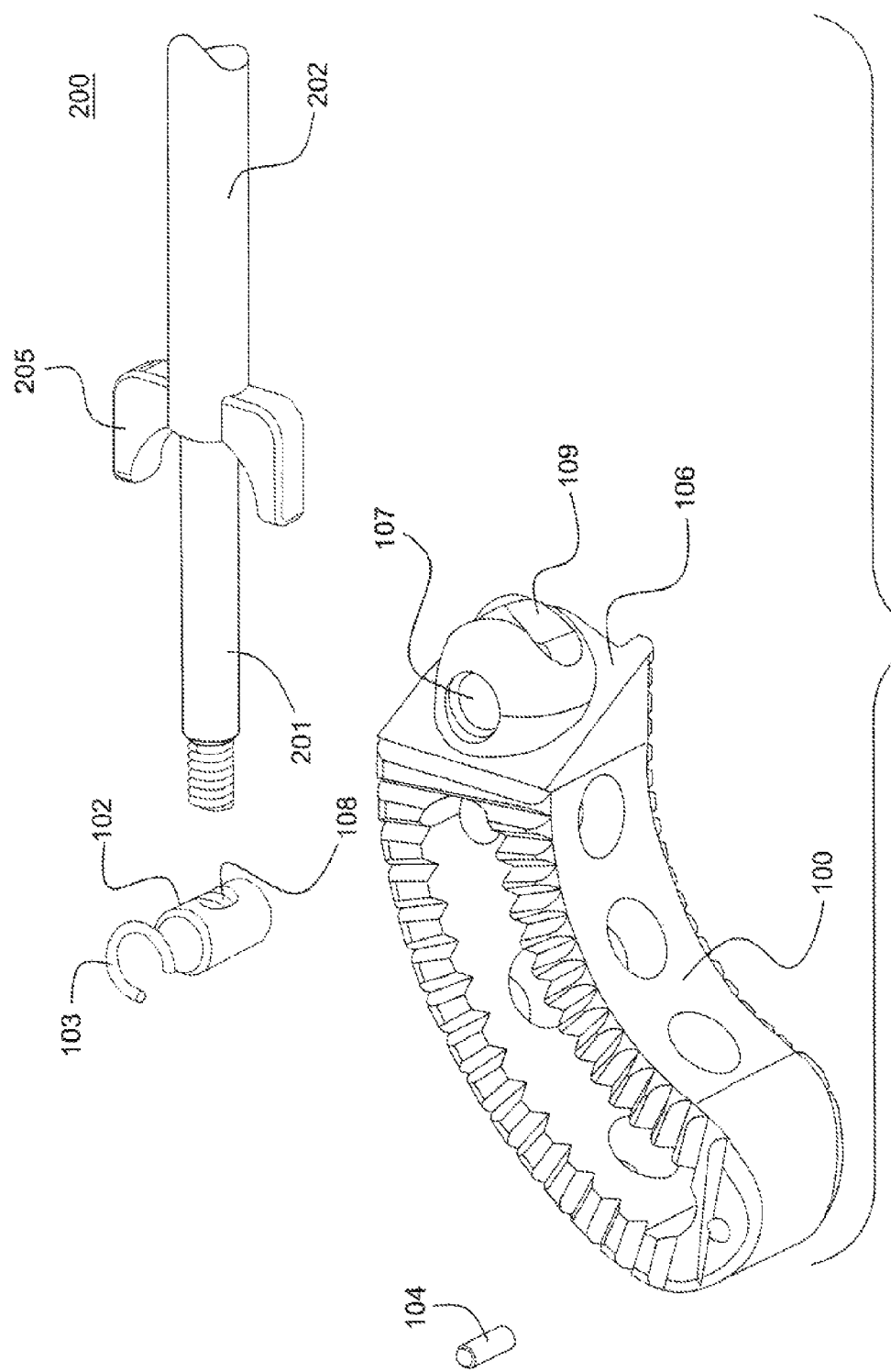
FIG. 2 is an exploded view showing the spinal implant separate from the insertion instrument.

FIG. 2 shows the details of the attachment of the implant 100 to the instrument 200. Threaded pin 102 is inserted into the channel 107 in the spherical protrusion (mount) 105 and retained there by a snap ring 103. A threaded hollow shaft 108 in the threaded pin 102 is aligned with the slot opening 109 of the implant so that the treaded rod 201 can be threaded into the shaft 108 of the pin 102. Slot opening allows pivoting of the implant by accommodating the pendulum motion of the rod 201. Pin 104 is made of a material that enhances X-ray imaging. Making the pin visible assists the physician in the positioning of the implant while viewing a real-time x-ray image of the implant and vertebra.

The actuator 202 may be a hollow tube that is coaxial with the rod 201. The pushers are fixed to the distal end of the actuator. The pushers 205 include cams that engage a cam surface 106 on the implant. The proximal end of the tube has a knob (e.g. actuator wings) 206 to turn the tube and thereby move the cams against the cam surface. The angle of the implant with respect to the actuator is adjusted by moving the cam against the cam surface. Adjusting the angle may allow the surgeon to properly place the implant in the spine area.

Figure 3:
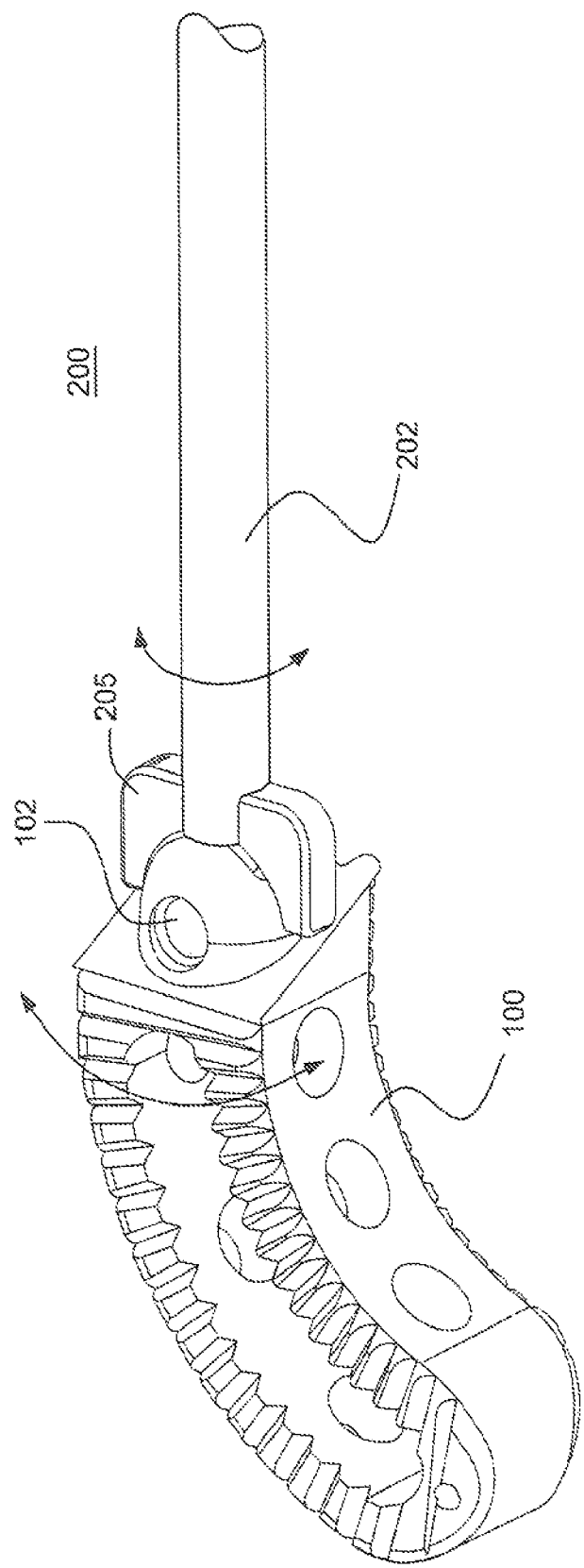
FIG. 3 is a perspective view of the FIG. 3 illustrates the interaction between the actuator 202 of the instrument and the implant 100.

FIG. 3 illustrates the interaction between the Actuator 202 of the instrument and the implant 100. The actuator 202 is rotated around the axis of the threaded rod 201 that is engaged in the threaded pin 102. As the cammed pushers 205 rotate, they push against the surface 106. As a result the implant 100 turns around the axis of the pin 102. It can be envisioned as if the implant is performing a "dog wagging its tail" motion with respect to the insert instrument 200.

If the locking knob 207 (FIG. 1) is rotated, the actuator 202 is pushed against the implant 100. Both pushers are advanced towards the surface 106 to bind the actuator against the implant so as to lock the implant with respect to the instrument. When locked, the assembly of the implant and instrument can be advanced while retaining the desired angle of the implant 100 in relation to the insertion instrument 200.

Figure 4:
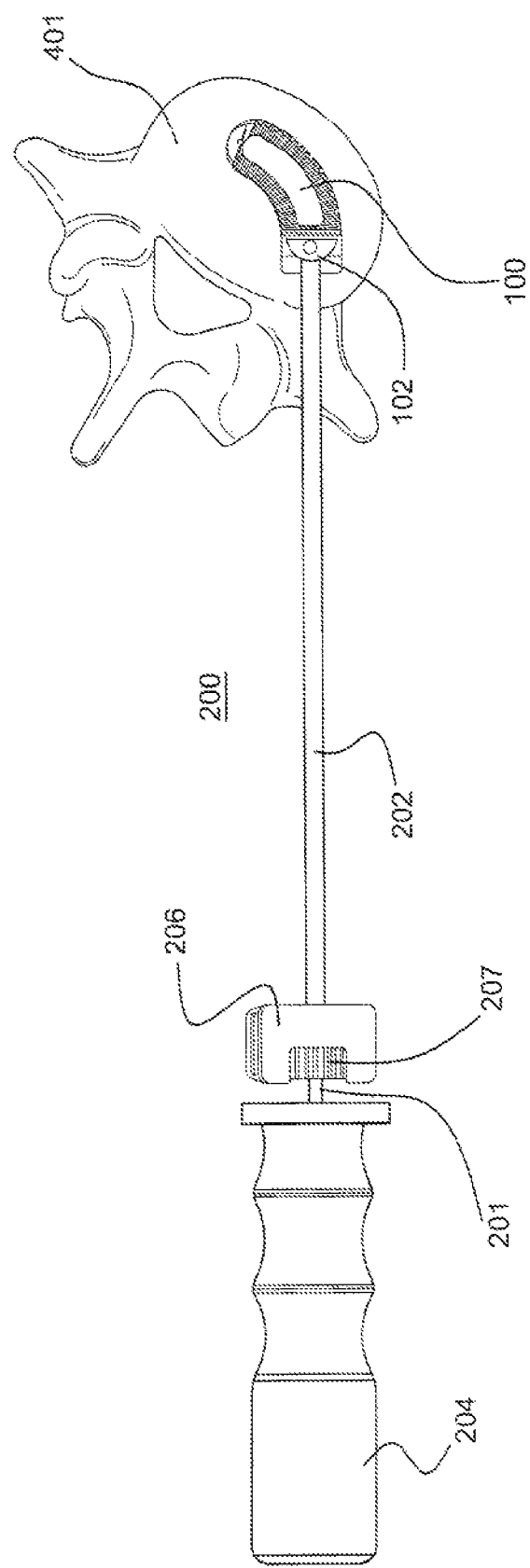
FIG. 4 is a perspective view of the implant releasably attached to the insertion instrument and positioned over a vertebra.

FIG. 4 shows the implant 100 with the insertion instrument 200 attached and in position on a patient vertebra 401. Rotation of the actuator 202 in relation to the axis of the threaded rod 201 results in the rotation of the implant 100 around the axis of the pin 102. Rotation of the knob 207 pushes the actuator 202 into the implant locking the assembly. When the assembly is locked hammer tapping can be applied to the handle 204 to advance the assembly forward.

FIGS. 5A, 5B, 5C, 5D and 5E show a side view of a first alternative spinal implant tool 500 to insert a spinal implant 502. The tool has a handle 504 at a proximal end, a center rod that connects to a pin or other attachment to the spinal implant, such as rod 201 and pin 102 shown in FIG. 2, and a hollow rod 506 that serves as an actuator rod similar to rod 201 in FIGS. 1 to 3. The center rod may be turned from the handle by a turn knob 508 to rotate the spinal implant about the axis of the rod. The actuator rod 506 may be turned at the handle by a winged grip 510 to rotate the cam surface 512 at the distal end of the actuator rod. Rotating the actuator and cam surface causes the pivot yaw in a pivoting movement illustrated in FIG. 3.

The cam surface 512 is a flat annular surface on a cylindrical metal section 514 attached to the distal end of the rod 506. The cam surface 512 is in a plane offset from a plan perpendicular to the axis of the rod. The degrees of the offset may vary depending on the amount of yaw movement desired by the spinal implant, but is preferably in a range of 5 degrees to 25 degrees. The cam surface 512 abuts bull-nose surfaces 516 at the end of a ridge 518 at the end of the spinal implant 502. The bull-nose surfaces 518 may be on opposite sides of a hemispherical attachment structure 519 that receives the end of the center rod and releasable pin that temporarily secures the implant to the tool.

The bull-nose surfaces slide against the cam surface 512 as that surface and its rod rotate with respect to the inner rod that is attached to implant. As the bull-nose surfaces slide against the cam surface, the spinal implant moves in a yaw direction. The yaw movement of the implant is controlled by the surgeon twisting the winged grip 510 at the handle. To assist the surgeon in determining the yaw orientation of the implant, a shallow groove 520 may be machined in the cam surface. The surgeon will feel in his fingers in the winged grip the action of the bull nose surfaces sliding across the groove. Knowing when the spinal implant is in the yaw orientation corresponding to the grooves 520 gives the surgeon information helpful in positioning the spinal implant in the spine. Further, the grooves 512 may be used to lock the yaw position of the spinal implant by applying sufficient compressive force between the bull nose surfaces and cam surface. The compressive force may be adjusted by turning the rod so that its threaded end turns into or out of the pin in the hemispherical structure 519.

Figure 6A:
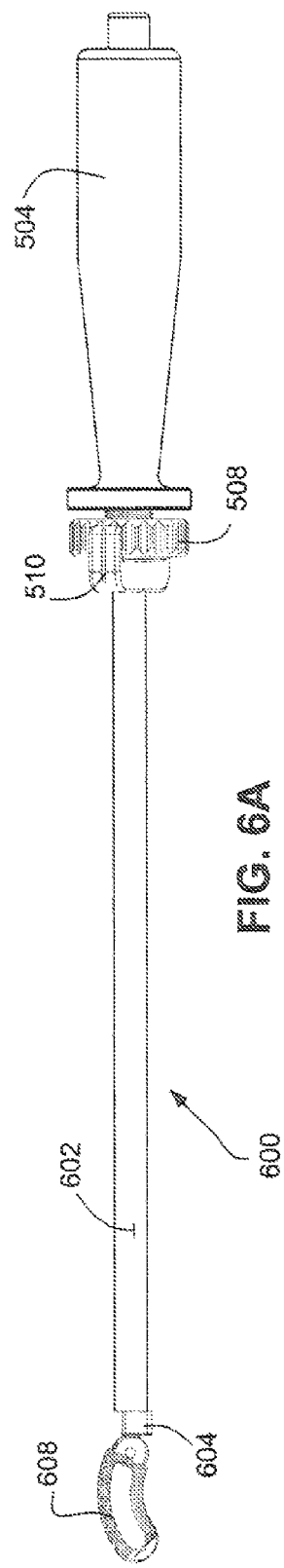
FIGS. 6A, 6B and 6C show a side view of an second alternative spinal implant tool (FIG. 6A), a perspective view of the distal end of tool attached to a spinal implant (FIG. 6B), and a second perspective view of the distal end of tool attached to a spinal implant (FIG. 6C).
Figure 6B:
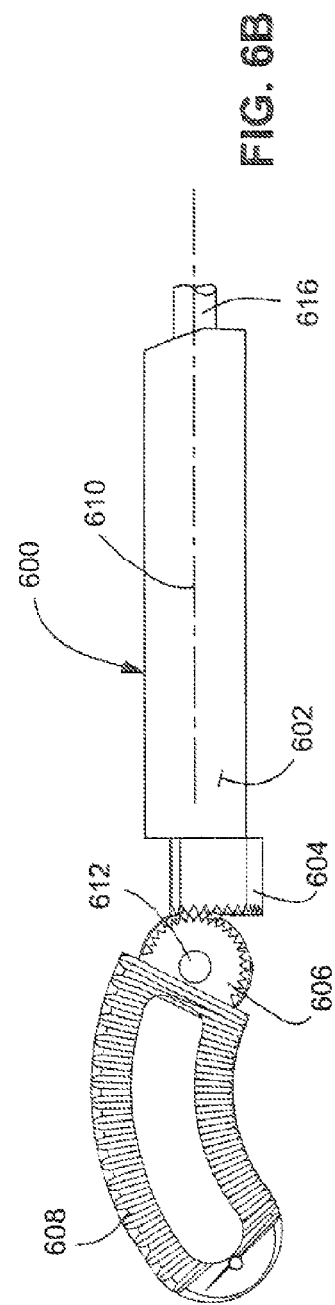
Figure 6C:
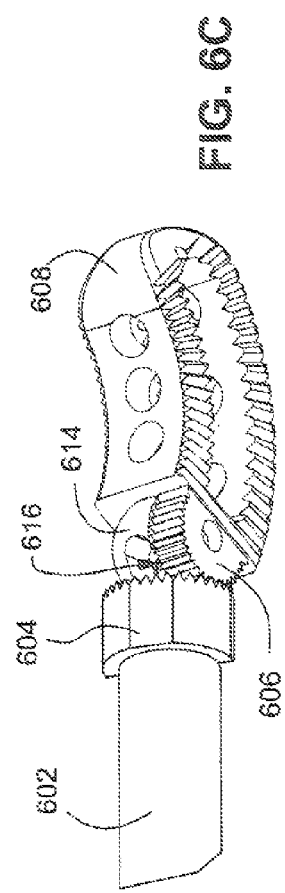

FIGS. 6A, 6B and 6C show views of second alternative spinal implant tool 600 having many components similar to the tool 500 shown in FIG. 5A. These similar components are labeled with the same reference numbers as used in FIG. 5A and the corresponding text description of the tool given for FIG. 5A applies to tool 600. The distal end of the of the actuator rod 602 includes a gear actuator 604 that engages gear teeth on a semi-circular gear attachment 606 on the spine implant 608. The gear actuator 604 make by half-circle gear extending partially, e.g., half-way, around the axis 610 of the rod 602. The engagement of the teeth of the gear 604 with the teeth of the attachment 606 on the implant 608 causes the implant to pivot about pin 612 coupled to a hemispherical attachment 614 (similar to hemispherical attachment 519) and engaging a threaded end of the center rod 616 of the tool. The gear attachment 606 is on the end of the implant and offset from the hemispherical attachment 614.

Due to the engagement between the gear teeth of the gear attachment 606 on the implant and the gear actuator 604 on the actuator, the surgeon can turn the wing grip 510 on the actuator rod to cause the implant to yaw back and forth respect to the axis 610 of the tool 600. Turing the actuator rod approximately 180 degrees causes the gear teeth on the gear attachment 606 to disengage and rotate away from the gear actuator 604. Further, yaw movement of the implant can be prevent by turning locking knob 510 that the geared actuator 604 is forced into the gears of the geared to bind against the gear teeth in the gear attachment creating sufficient friction to prevent implant rotation in the yaw directions.

FIGS. 7A and 7B show a third alternative spinal implant tool 700 having many components similar to the tool 500 shown in FIG. 5A. These similar components are labeled with the same reference numbers as used in FIG. 5A and the corresponding text description of the tool given for FIG. 5A applies to tool 600. The center rod 702 may have a threaded end that engages a pin 704 mounted in a hemispherical attachment 708 (similar to hemispherical attachment 519) at the end of the spinal implant 706. The end of the implant with the hemispherical attachment has a slanted surface 710. The distal end of the actuator rod 712 includes a pair of legs 714 each having a bull-nose end surface 716 that slides against the slanted surface at the end of the spinal implant. The rotation of the wing grip 510 at the handle end 504 of the tool 700 turns the actuator shaft 712 and causes the bull-nose end surfaces 716 to slide against the slanted surface 708 of the implant. The sliding movement of the bull-nose end surface against the surface 708 pivots the implant in a yaw movement with respect to the axis of the tool.

The spinal insertion tool may be used to prepare a space for an implant between adjacent vertebra. The tool 700 provides a steerable tool having detachable tips. These tips may include, but not limited to, interchangable rasps, curettes, broaches, osteotomes, reamers, dissectors and implant trial sizes. The interchangeable instrument tips are steered and released by any method or combination of methods described above.

The slanted surface 710 may be included in a wedge attachment 718 attached by a bracket 720 on the end of the implant 706. The wedge attachment may be secured to the implant prior to surgery and before the implant is inserted into the spine of a patient. The wedge attachment may be interchangeable with other attachments to the spinal implant, such as wedges with slanted surfaces of varying angles to provide variable sweep of the yaw movement. In addition, the wedge attachment may be used secured to surgical rasps, curettes, spoons, picks, scrapers and other surgical tools. The wedge attachment allows a variety of surgical tools to be mounted on the end of the spinal implant tool which, with these tools, can perform surgical functions, e.g., removing bone, spinal disc and other material from a disc region of the spine, smoothing a spine surface to later receive a spinal implant and to clear away material from the disc region. Accordingly, the spinal tool may be used for surgical procedures in addition to implanting a spinal insert and steering the insert during its insertion into the spine.

A spinal implant may be used to stabilize a portion of a spine. The implant may promote bone growth between adjacent vertebra that fuses the vertebra together. An implant may include an opening through a height of a body of the implant. The body of the implant may include curved sides. A top and/or a bottom of the implant may include protrusions that contact and/or engage vertebral surfaces to prevent backout of the implant from the disc space.

A spinal implant may be used to provide stability and promote fusion of adjacent vertebra. The implant may be used in conjunction with a spinal stabilization device such as a bone plate or rod-and-fastener stabilization system. The implant may establish a desired separation distance between vertebra. The implant may promote bone growth between adjacent vertebra that fuses the vertebra together. Instrument at is necessary for insertion of an implant in a patient and alignment of the implant in the space.

A discectomy may be performed to establish a disc space between vertebra. The disc space may be prepared for implant insertion by distraction of adjacent vertebra, rasping and filing of the bone to achieve the desired spacing. It is desired to perform insertion of the implant and positioning of the implant using minimum number of inserted instruments and thought the smallest possible insertion channel in the body.

Implants may be constructed of biocompatible materials sufficiently strong to maintain spinal distraction. Implants may include, but are not limited to, allograft bone, xenograft bone, autograft bone, metals, ceramics, inorganic compositions, polymers such as PEEK, or combinations thereof. If the implant is not made of bone, surfaces of the implant that contact bone may be treated to promote fusion of the implant to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces.

FIGS. 8A, 8B and 8C show a perspective view (FIG. 8A), a tope view (FIG. 8B) and an inner side view (FIG. 8C) of a spinal implant 800 formed of a polymer (PEEK) implant body and including of a metallic ball 802. The ball may be formed of titanium and inserted in a hemispherical recess 804 of the end 806 of the implant 800 For example, the end section 806 of the implant may be a wedge having an inner chamber to receive and hold the ball 802. The wedge 806 is secured to an end surface 808 of the body 810 of the implant. The wedge, when secured to the body, holds the ball 802 on the implant and allows the ball to pivot with the threaded end of the spinal implant tool. The ball may be hollow and have a cylindrical aperture 812 to receive a pin. The pin (see FIG. 2) has a threaded side aperture to receive a threaded end of the centre rod of a spine insertion tool. The ball 802, and preferably the wedge 806, are formed of a metal (such as Titanium) for strength. The body 810 of the implant may be formed of an alternate material, such as a radiolucent polymer (including, but not limited to, PEEK).

In some embodiments, an implant may include an opening that extends through a body of the implant. The opening may have a regular shape or an irregular shape. Bone graft may be placed in the opening. The bone graft may be autogenic bone graft, allogenic bone graft, xenogenic bone graft, and/or synthetic bone graft. Some implant embodiments may be constructed from allogenic bone, such as cortical bone from a femur, tibia, or other large bone. In some embodiments, an implant may be formed from one or more pieces of allograft bone cut to a desired shape.

In certain embodiments, sides of an implant may be shaped to increase contact between an implant and adjacent vertebra with notches, ribs and other similar features. Increasing contact of an implant with adjacent vertebra may inhibit movement of the implant after insertion. An increased contact area between an implant and adjacent vertebra may promote bone growth between adjacent vertebra.

In some embodiments, one or more sides of an implant may be curved. One or more curved sides of an implant may allow the implant to be maneuvered in a disc space during insertion of the implant. The curvature of a side may approximate a curvature of an anterior side of a vertebra adjacent to which the implant is inserted.

An instrument may be used to insert an implant in a prepared space. Instruments may be supplied to a surgeon or surgical team in an instrument set. An instrument set may include one or more implants for use during an insertion procedure. An instrument set may include implants of various sizes and/or lordotic angles to allow selection of an implant to suit a patient during surgery. Instrument is attached to the implant before the insertion into the body. When the desired position of the implant is achieved, instrument is disengaged from the implant and can be extracted from the body.

An instrument acts as an implant inserter. The implant inserter may be used to push the implant and to rotate the implant. After insertion of the implant, the implant may be released from the inserter without the application of significant repositioning forces to the implant. It can be imagined that the insertion instrument can be screwed into the implant using threads or use other techniques such as a tightening collet, jamming or grabbing. In the disclosed embodiment the implant turns around the axis of the implant pin as a result of the rotation of cam pushers. It can be imagined that other mechanisms can be used to rotate the implant such as ratchets or threaded push rods. The implant inserter may have a low profile that allows for visualization of the implant and surrounding area during insertion of the implant. Implant is equipped to couple and uncouple from the instrument.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A spinal implant comprising:
   a top, wherein at least a portion of the top is configured to contact a first vertebra;
   a bottom, wherein at least a portion of the bottom is configured to contact a second vertebra;
   a side having a releasable attachment to receive an insertion device, wherein the attachment has a pivot axis about which the implant pivots and the side is between the top and bottom,
   a housing having a curved surface on the side curved in orthogonal planes and the releasable attachment is within the housing,
   a slot in the curved surface of the housing through which the insertion device extends to reach the releasable attachment, and
   ridges on opposite sides of the curved surface of the housing, wherein the ridges have an outer surface to engage a cam surface of the insertion device.

2. The spinal implant in claim 1 wherein the pivot axis is coaxial to a pin in the attachment, and wherein the insertion device attaches to the pin.

3. The spinal implant in claim 1 wherein the pivot axis is oblique to an axis of the insertion device.

4. The spinal implant in claim 1 wherein the implant further comprises a bull nose surface at the ridges.

5. A spinal implant comprising:
   a top, wherein at least a portion of the top is configured to contact a first vertebra;
   a bottom, wherein at least a portion of the bottom is configured to contact a second vertebra;
   a curved surface on a side of the spinal implant and between the top and bottom, wherein the curved surface is curved in orthogonal planes;
   a pivot pin in the spinal implant and accessible through a slot in the curved surface, and
   at least one projection adjacent the curved surface wherein the projection engages a cam surface of a spinal insertion tool.

6. The spinal implant in claim 5 wherein a pivot axis of the spinal implant is coaxial to the pivot pin.

7. The spinal implant in claim 5 wherein the at least one projection is a pair of ridges on opposite sides of the curved surface.

8. The spinal implant in claim 5 wherein the curved surface is at least partially hemispherical.

9. The spinal implant in claim 5 wherein the implant pivots about the pivot pin.

10. The spinal implant of claim 5 wherein the curved surface includes an aperture to receive the pivot pin.

11. A spinal implant comprising:
    a top, wherein at least a portion of the top is configured to contact a first vertebra;
    a bottom, wherein at least a portion of the bottom is Configured to contact a second vertebra;
    a side of the spinal implant having a housing with at least a partially hemispherical outer surface;
    a pin mounted within the housing, wherein the pin is accessible through a slot in the housing and the slot is in the at least partially hemispherical outer surface, and
    at least one projection on the side and adjacent the hemispherical outer surface, wherein the projection engages a cam surface of a spinal insertion tool.

12. The spinal implant of claim 11 wherein the pin includes a threaded aperture.

13. The spinal implant in claim 11 wherein a pivot axis of the spinal implant is coaxial to the pivot pin.

14. The spinal implant in claim 11 wherein the at least one projection is a pair of ridges on opposite sides of the at least partially hemispherical outer surface.

15. The spinal implant in claim 11 wherein the at least partially hemispherical outer surface has a surface which is at a common radius from a center of the housing.

16. The spinal implant in claim 11 wherein the pivot axis is coaxial to the pivot pin.

17. The spinal implant in claim 11 wherein the implant pivots about the pivot pin.

18. The spinal implant of claim 11 wherein the housing includes an aperture to receive the pivot pin.

* * * * *